US012791514B2

(12) United States Patent
Fujimoto et al.

(10) Patent No.: US 12,791,514 B2

(45) Date of Patent: Nov. 10, 2026

(54) ELECTROCHEMICAL DEVICE, SENSOR, AND SENSOR SYSTEM

(71) Applicant: KABUSHIKI KAISHA TOSHIBA, Tokyo (JP)

(72) Inventors: Akira Fujimoto, Kawasaki Kanagawa (JP); Yosuke Akimoto, Yokohama Kanagawa (JP); Hiroaki Yamazaki, Yokohama Kanagawa (JP)

(73) Assignee: KABUSHIKI KAISHA TOSHIBA, Kawasaki Kanagawa (JP)

( * ) Notice: Subject to any disclaimer, the term of this patent is extended or adjusted under 35 U.S.C. 154(b) by 248 days.

(21) Appl. No.: 18/433,992

(22) Filed: Feb. 6, 2024

(65) Prior Publication Data

US 2024/0302320 A1 Sep. 12, 2024

(30) Foreign Application Priority Data

Mar. 10, 2023 (JP) ................................. 2023-037434

(51) Int. Cl.

*G01N 27/407* (2006.01)
*G01N 27/409* (2006.01)
*G01N 33/00* (2006.01)

(52) U.S. Cl.

CPC ....... *G01N 27/4077* (2013.01); *G01N 27/409* (2013.01); *G01N 33/0027* (2013.01)

(58) Field of Classification Search

CPC ............. G01N 27/4077; G01N 27/409; G01N 33/0027

See application file for complete search history.

(56) References Cited

U.S. PATENT DOCUMENTS

| | | | | |
|---|---|---|---|---|
| 2005/0212174 | A1 | 9/2005 | Tanahashi et al. | |
| 2011/0259813 | A1 | 10/2011 | Wertz et al. | |
| 2014/0030179 | A1 | 1/2014 | Miller, III | |
| 2016/0116404 | A1 | 4/2016 | Bertaux | |
| 2017/0038229 | A1* | 2/2017 | Kshirsagar | G01N 29/036 |
| 2017/0038343 | A1* | 2/2017 | Kshirsagar | G01N 29/2425 |
| 2017/0102352 | A1* | 4/2017 | Scheffler | G01N 33/497 |
| 2018/0087794 | A1* | 3/2018 | Bahar | C25B 9/73 |
| 2020/0324510 | A1 | 10/2020 | Yung et al. | |
| 2021/0088465 | A1 | 3/2021 | Tsuboi et al. | |

(Continued)

FOREIGN PATENT DOCUMENTS

| | | | |
|---|---|---|---|
| JP | 62-51269 | U1 | 3/1987 |
| JP | 63-70067 | U1 | 5/1988 |

(Continued)

OTHER PUBLICATIONS

Tang, Fan basics: air flow, static pressure and impedance, https://blog.orientalmotor.com/fan-basics-air-flow-static-pressure-impedance, Last updated on Sep. 20, 2021 (Year: 2021).*

(Continued)

*Primary Examiner* — Shizhi Qian

(74) *Attorney, Agent, or Firm* — Finnegan, Henderson, Farabow, Garrett & Dunner, LLP

(57) ABSTRACT

An electrochemical device includes a housing, a first member and a second member provided between the housing and the first member. The housing has a first through hole including a first opening that faces the first member. The second member has a second through hole including a second opening.

5 Claims, 5 Drawing Sheets

(56) References Cited

U.S. PATENT DOCUMENTS

| | | | | |
|---|---|---|---|---|
| 2021/0214854 | A1* | 7/2021 | Chapples ........... | G01N 27/4045 |
| 2024/0082764 | A1 | 3/2024 | Fujimoto et al. | |

FOREIGN PATENT DOCUMENTS

| | | | |
|---|---|---|---|
| JP | 2002-221505 | A | 8/2002 |
| JP | 2014-2045 | A | 1/2014 |
| JP | 2014-221933 | A | 11/2014 |
| JP | 2015-199335 | A | 11/2015 |
| JP | 2015-219148 | A | 12/2015 |
| JP | 2017-227514 | A | 12/2017 |
| WO | WO 2020/003465 | A1 | 1/2020 |

OTHER PUBLICATIONS

Japan Patent Office, Office Action in JP App. No. 2023-037434 (Jan. 9, 2026).

* cited by examiner

ELECTROCHEMICAL DEVICE, SENSOR, AND SENSOR SYSTEM

CROSS-REFERENCE TO RELATED APPLICATIONS

This application is based upon and claims the benefit of priority from Japanese Patent Application No. 2023-037434 filed on Mar. 10, 2023, and the entire contents of which are incorporated herein by reference.

FIELD

Embodiments described herein relate generally to an electrochemical device, a sensor, and a sensor system.

BACKGROUND

For example, there is a sensor that senses oxygen and hydrogen.

In such a sensor, generally, the sensor is exposed to vapor, gas, and the like in the atmosphere in which the sensor is installed, so that a sensing function is deteriorated.

DETAILED DESCRIPTION

Figure 1:
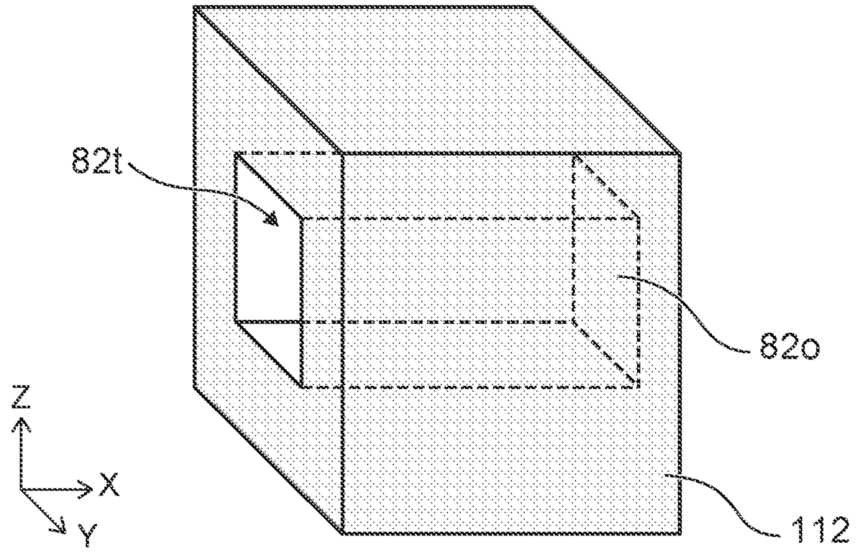
FIG. 1 is a schematic perspective view illustrating a second through hole and a second opening of a second member.

Hereinafter, embodiments will be described with reference to the drawings.

In the following description, components that exhibit the same or similar functions are denoted by the same reference numerals throughout all the drawings, and redundant description will be omitted.

Note that each drawing is a schematic view for promoting the description of an embodiment and the understanding thereof, and points regarding the shape, size, ratio, and the like may be different from those of the actual device, but the design of these points can be appropriately modified in consideration of the following description and known techniques. In addition, in the present specification and each drawing, the same elements as those described above with respect to the previously described drawings are denoted by the same reference numerals, and a detailed description thereof is appropriately omitted.

First Embodiment

A sensor that senses oxygen or hydrogen may be contaminated, thereby deteriorating a sensing function or causing a sensor circuit included in the sensor to fail. The sensor may be contaminated by exposure to moisture, gas, and the like in an atmosphere in which an electrochemical device is provided. Among the contaminations, for example, in order to suppress the contamination of the sensor by moisture (hereinafter, referred to collectively as water vapor, but an aspect may be liquid or gas), the electrochemical device includes an electrochemical element such as a dehumidifier. However, when an amount of water vapor entering the inside of the electrochemical device exceeds a dehumidifying effect by the electrochemical element, the sensor is contaminated and the sensing function is deteriorated. Therefore, it is necessary to suppress water vapor from entering the inside of the electrochemical device, to suppress deterioration of the sensing function of the sensor, and to suppress failure due to exposure of the sensor circuit of the sensor to water vapor for a long time.

Therefore, according to a first embodiment, there is provided an electrochemical device having a housing, a first member, and a second member provided between the housing and the first member, in which the housing has a first through hole including a first opening and facing the first member, and the second member has a second through hole including a second opening.

Hereinafter, the electrochemical device that suppresses deterioration of the sensing function in the sensor will be described with reference to the drawings. FIG. 1 is a schematic perspective view illustrating the second through hole and the second opening of the second member. In FIG. 1, a second member 112 has a second through hole 82*t*, and the second through hole 82*t* has a second opening 82*o*. The second opening 82*o* corresponds to an inlet or an outlet of the second through hole 82*t*. In FIG. 1, the second opening 82*o* is represented by a substantially quadrangular shape, but the shape is not limited.

In FIG. 1, an area of the second opening 82*o* is equal to an area of a cross-section when the second through hole 82*t* is cut along a YZ plane, but may be different.

Although not illustrated, the first through hole and the first opening are included in the housing to be described later, and when the second member 112 is the housing in FIG. 1, the first through hole corresponds to the second through hole 82*t* and the first opening corresponds to the second opening 82*o*.

Figure 2:
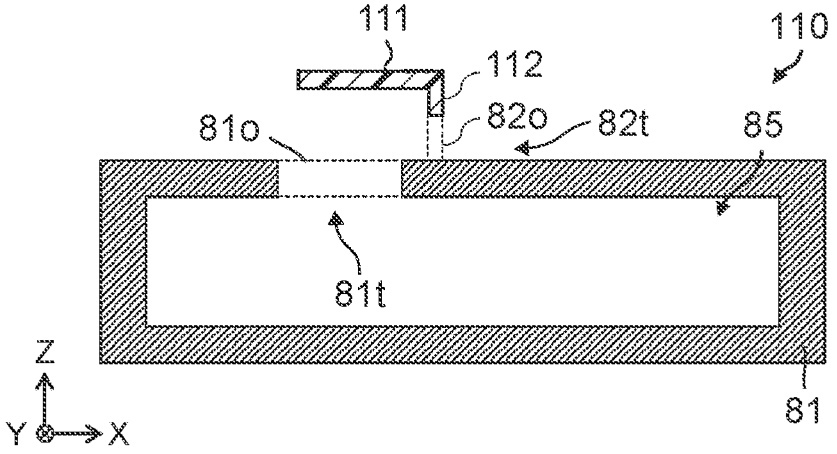
FIG. 2 is a schematic cross-sectional view illustrating an electrochemical device according to a first embodiment.

FIG. 2 is a schematic cross-sectional view illustrating the electrochemical device according to the first embodiment. In FIG. 2, an electrochemical device 110 has a housing 81 and the second member 112 provided between the housing 81 and a first member 111. The housing 81 has a first through hole 81*t* including a first opening 81*o* and facing the first member 111. The second member has the second through hole 82*t* including the second opening 82*o*. In FIG. 2, a normal direction of the first opening 81*o* is defined as a Z-axis direction, a direction perpendicular to the Z-axis direction is defined as an X-axis direction, and a direction perpendicular to the Z-axis and the X-axis is defined as a Y-axis.

The first member 111 is provided above the housing 81. The first member 111 is positioned such that the first opening 81*o* faces the first member 111. The thing that the first opening 81*o* faces the first member 111 means that when the first opening 81*o* is projected in the normal direction of the first opening 81*o*, at least a part of a region where the first opening 81*o* and the first member 111 overlap exists. At least a part of the first opening 81*o* and a part of the first member 111 face each other. For example, in FIG. 2, the housing 81 and the first member 111 are represented by substantially quadrangular shapes, and the first member 111 has the region partially overlapping the first opening 81*o* when viewed along the Z-axis direction which is the normal direction of the first opening 81*o*. Alternatively, for example, even when the first member 111 has a cross-section such as a half-elliptical shape, in the present embodiment, when the first opening 81*o* is projected in the normal direction of the first opening 81*o*, there exists the region where the first opening 81*o* and the first member 111 overlap each other. Preferably, the first member 111 completely covers the first opening 81*o*. That is, when both the first opening 81*o* and the first member 111 are projected in the normal direction of the first opening 81*o*, it is preferable that the projected first member 111 includes the projected first opening 81*o*. In the preferable case described above in FIG. 2, the length of the first member 111 in the X-axis direction is equal to or longer than the length of the first opening 81*o* in the X-axis direction. In addition, although not illustrated in FIG. 2, the same applies to the Y-axis direction, and the length of the first member 111 in the Y-axis direction is preferably equal to or longer than the length of the first opening 81*o* in the Y-axis direction.

When viewed along the Z-axis direction, since at least a part of the region where the first opening 81*o* and the first member 111 overlap each other exists, an amount of water vapor from the outside to the inside of the housing 81 in a vicinity of the first opening 81*o* can be suppressed. For example, water vapor entering the inside of the housing 81 through the first opening 81*o* in the Z-axis direction is blocked by the first member 111.

The second member 112 has the second opening 82*o*. At least a part of the second member 112 is provided on the housing 81. The second member 112 may be integrated with the housing 81. For example, the second member 112 may be integrated with the housing 81, for example, the second member 112 may be joined with the housing 81.

The second member 112 may be integrated with the first member 111. For example, the second member 112 may be joined with the first member 111. When the housing 81 is substantially quadrangular, the second member 112 may be provided in a direction intersecting a surface of the housing 81 where the first opening 81*o* exists. In FIG. 2, the second member 112 having the second opening 82*o* is in contact perpendicularly with the surface of the housing 81 where the first opening 81*o* exists, but may be provided on the surface of the housing 81 where the first opening 81*o* exists, and may not necessarily be provided perpendicularly. Since the second opening 82*o* exists in the second member 112, for example, when the second opening 82*o* is provided in the X-axis direction, water vapor flowing in the X-axis direction can flow in the X-axis direction without being blocked by the second member 112. As a result, an amount of water vapor that is blocked by the second member 112 and enters the inside of the housing 81 from the first opening 81*o* can be suppressed.

Figure 3:
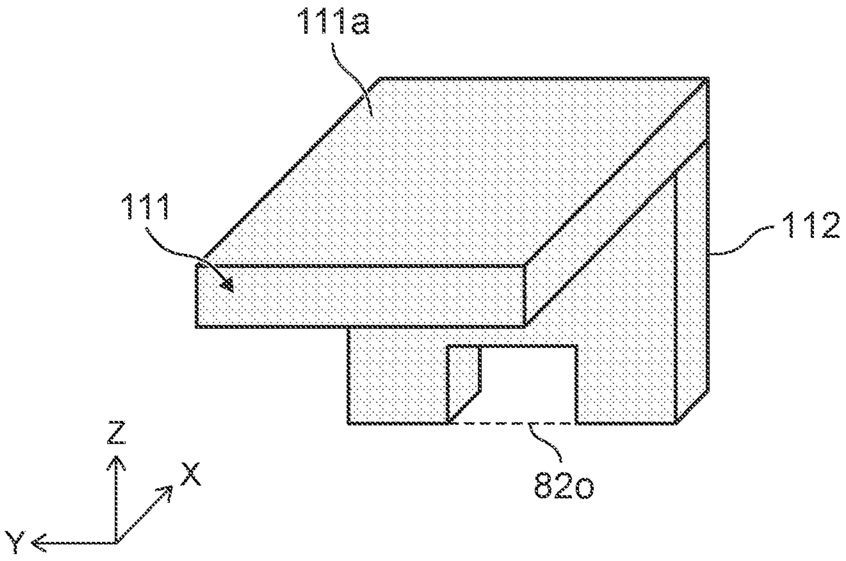
FIG. 3 is a schematic perspective view illustrating an example of a first member and the second member included in the electrochemical device according to the first embodiment.

FIG. 3 is a schematic perspective view illustrating an example of the first member and the second member included in the electrochemical device according to the first embodiment. FIG. 3 represents the first member 111 and the second member 112 illustrated in FIG. 2, as illustrated in FIG. 3 in the respective directions of the X axis, the Y axis, and the Z axis. In FIG. 3, the first member 111 is parallel to an X-Y plane and is parallel to the surface of the housing where the first opening exists, but the first member 111 is not necessarily parallel to the surface of the housing described above. In addition, in FIG. 3, the first member 111 is represented by a substantially rectangular parallelepiped, but the shape is not necessarily a substantially rectangular parallelepiped, and may be, for example, a shape such as a dome shape or a bell shape that is high at a central portion of the first member 111 and has a downward gradient toward a peripheral end portion. The existence of the first member 111 makes it possible to suppress the amount of water vapor entering the inside of the housing from the outside of the housing in the vicinity of the first opening. The length of a side of the first member 111 in the X-axis direction is preferably longer than the length of a side of the first opening in the X-axis direction. This is because the side of the first member 111 in the X-axis direction is longer than the first opening, so that water vapor can be prevented from entering the inside of the housing from the Z-axis direction. In addition, the length of a side of the first member 111 in the Y-axis direction is preferably longer than the length of a side of the first opening in the Y-axis direction. As a result, the amount of water vapor flowing from the outside of the housing to the inside of the housing in the vicinity of the first opening can be further suppressed.

The first member 111 has a lower surface facing the housing and an upper surface 111*a* facing the lower surface. When viewed in the Z-axis direction, the lower surface of the first member 111 exists between the upper surface 111*a* of the first member 111 and the housing. When the lower surface of the first member 111 faces the housing, this means that when the lower surface and the housing are projected in a normal direction of the lower surface, at the very least, overlapping portions of the projected regions exist.

In FIG. 3, the second member 112 is parallel to the YZ plane and is provided perpendicular to the surface of the housing where the first opening exists. The second member 112 is not necessarily required to be parallel to the YZ plane or perpendicular to the surface of the housing where the first opening exists. The second member 112 has the second opening 82*o*. In FIG. 3, only one second opening 82*o* exists on the second member 112, but two or more second openings 82*o* may exist, such as a third through hole having a third opening and a fourth through hole having a fourth opening. In addition, the second opening 82*o* is represented by a substantially quadrangular shape in FIG. 3, but the shape thereof is not limited.

In FIG. 3, the second member 112 does not exist between the second opening 82*o* and the housing, that is, the second opening 82*o* exists at a peripheral end portion of the second member 112, but for example, the second opening 82*o* may exist near a central portion of the second member 112 as illustrated in FIG. 1.

The width of the second opening 82*o* in the Y-axis direction may be smaller or larger than the width of the first opening in the Y-axis direction.

Figure 4:
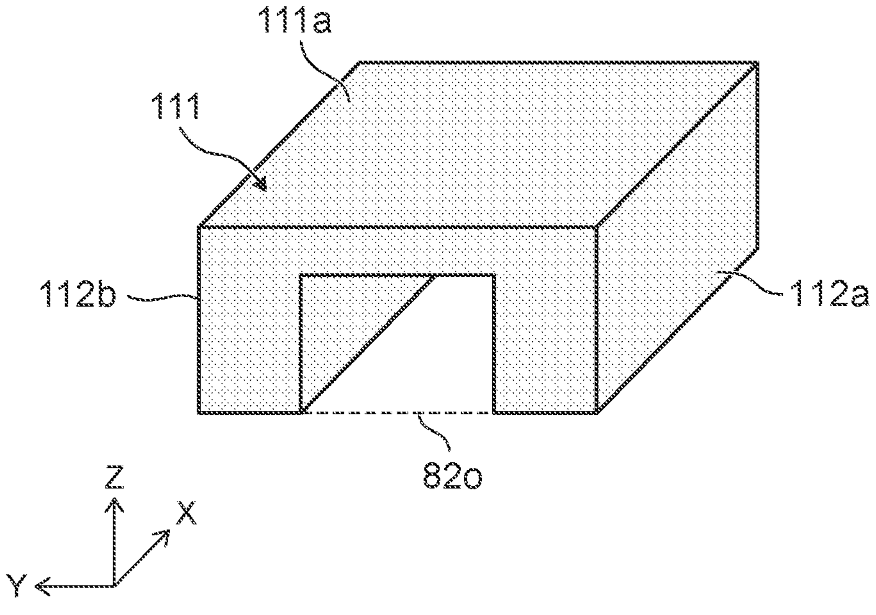
FIG. 4 is a schematic perspective view illustrating another example of the first member and the second member included in the electrochemical device according to the first embodiment.

FIG. 4 is a schematic perspective view illustrating another example of the first member and the second member included in the electrochemical device according to the first embodiment. In FIG. 4, the second member has a second a member 112*a* and a second b member 112*b*. The first member 111 in FIG. 4 is further integrated with the second a member 112*a* and the second b member 112*b* as compared with the first member 111 in FIG. 3.

The second a member 112*a* faces the second b member 112*b* and is provided perpendicular to the first member 111. Here, in FIG. 4, the second a member 112*a* and the second b member 112*b* are represented in a substantially rectangular parallelepiped, but regardless of the shape, for example, may have a shape in which at least one of the second a member 112*a* and the second b member 112*b* is high at a central portion and has a downward gradient toward a peripheral end portion, such as a dome shape or a bell shape.

Since the first member 111 is further integrated with the second a member 112*a* and the second b member 112*b* as compared with FIG. 3, for example, it is possible to further suppress the amount of water vapor entering the inside of the housing 81 from the second a member 112*a* side or the second b member 112*b* side toward the first opening.

The lengths of the sides of the first member 111 in the X-axis direction and the Y-axis direction with respect to the first opening are similar to those already described in FIG. 3, and thus are omitted.

In FIG. 4, the member in which the first member 111 and the second member are integrated shows a tunnel shape in which a part of a substantially rectangular parallelepiped penetrates in the X-axis direction, but the shape may be any shape, and for example, a shape in which a part of a dome-shaped three-dimensional body is penetrated in an X-axis direction or the Y-axis direction may be used.

Figure 5:
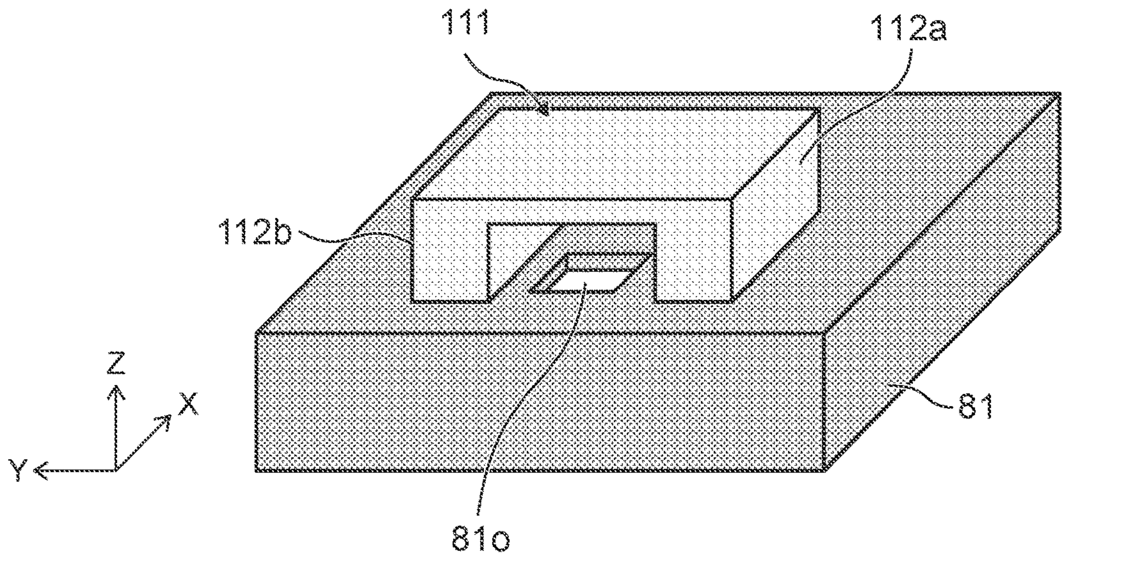
FIG. 5 is a schematic perspective view illustrating the electrochemical device having the first member and the second member of FIG. 4.

FIG. 5 is a schematic perspective view illustrating the electrochemical device having the first member and the second member in FIG. 4. In FIG. 5, the first member 111 is provided so that the first opening 81*o* faces the first member 111. The second through hole is desirably provided on the second member intersecting the surface of the housing 81 provided with the first opening 81*o*. For example, as illustrated in FIG. 5, one second through hole is provided on the second member, and there exists a flow path of wind in the X-axis direction, so that the amount of water vapor entering the inside of the housing 81 through the first opening 81*o* can be reduced. In addition, it is preferable that at least two or more second through holes exist, and for example, another similar second through hole along the X-axis direction may be provided. Alternatively, for example, as illustrated in FIG. 6 described later, the second member may have two different second through holes along the X-axis direction, and a space (S) may exist between the two second through holes. This makes it possible to suppress the amount of water vapor entering the inside of the electrochemical device from exceeding the amount of water vapor dehumidified by the electrochemical element. Therefore, it is possible to suppress deterioration or failure of the sensing function due to exposure of the sensor or the sensing circuit to water vapor for a long time. In the above, for example, a flow path of wind in the Y-axis direction may be provided by changing a place where the second through hole is provided on the second member.

Figure 6A:
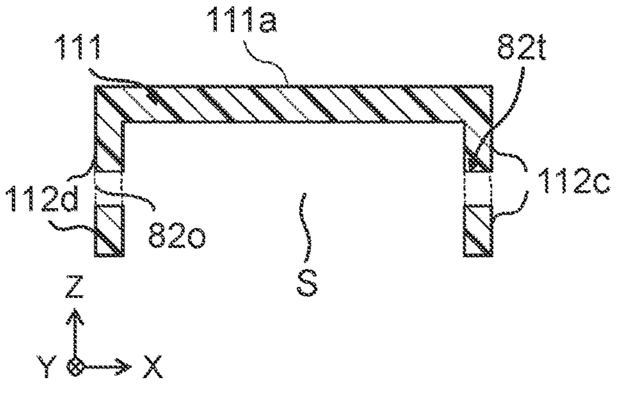
FIG. 6A and FIG. 6B are schematic cross-sectional views illustrating still another example of the first member and the second member included in the electrochemical device according to the first embodiment.
Figure 6B:
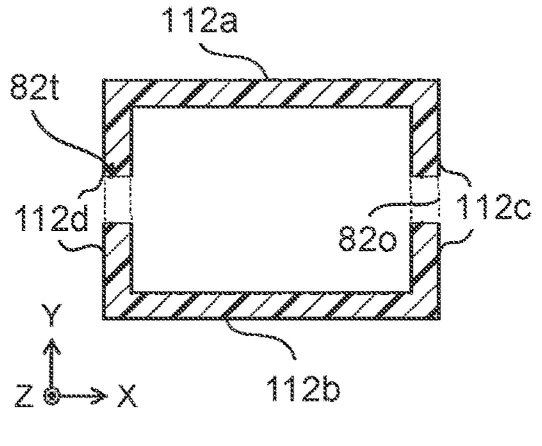

FIG. 6 illustrates still another example of the first member and the second member in FIG. 4. FIG. 6 is a schematic cross-sectional view illustrating still another example of the first member and the second member included in the electrochemical device according to the first embodiment. FIG. 6A is a cross-sectional view of the first member and the second member when cut along a ZX plane. FIG. 6B is a cross-sectional view of the first member and the second member of the same example when cut along the XY plane.

The second member in FIG. 6 further has a second c member 112*c* and a second d member 112*d* in addition to FIG. 4. The second d member 112*d* faces the second c member 112*c* and is provided perpendicular to the first member 111. Here, in FIG. 6, the second d member 112*d* and the second c member 112*c* are represented by a substantially rectangular parallelepiped, but may have any shape similar to the above-described second a member 112*a* and second b member 112*b*. By having the second c member 112*c* and the second d member 112*d*, for example, in FIG. 6, a cross-sectional area (corresponding to B described later) when the space (S) between the first member 111 and the housing including the first opening is cut along the YZ plane can be made larger than the area of the second opening 82*o* (corresponding to A described later). That is, when wind blows in the X-axis direction, the flow path of the wind can be narrowed at the second opening 82*o* which is the inlet and the outlet, and can be widened in the space sandwiched between the first member 111 and the housing. As a result, for example, the flow of water vapor coming from the X-axis direction can be slowed down. By slowing down the flow of water vapor, the amount of water vapor entering the inside of the housing through the first opening can be reduced, and deterioration of the dehumidifying effect by the electrochemical element can be suppressed.

There exist at least two or more second openings 82*o*. For example, one second opening 82*o* exists in each of the second d member 112*d* and the second c member 112*c*. As a result, a gas flow is generated in the X-axis direction which is the direction from the second d member 112*d* toward the second c member 112*c*, or a direction opposite to the X-axis direction, so that the gas is smoothly introduced.

The first member 111 has the lower surface facing the housing and the upper surface 111*a* facing the lower surface, and when the second opening 82*o* and the space between the upper surface 111*a* and the housing having the first opening are projected in the normal direction of the second opening 82*o*, the projected area of the second opening 82*o* is preferably 10% or more and 90% or less of the projected area of the above-described space. For example, in FIG. 6, the area in the YZ plane of the second opening 82*o*, which is the inlet or the outlet of the second through hole of the second member, is A. In addition, assuming that the area when the space between the upper surface 111*a* of the first member 111 and the housing having the first opening is projected in the normal direction of the second opening 82*o*, that is, in the X-axis direction in FIG. 6, is B, $(A/B)\times 100$ is preferably 10% or more and 90% or less. In addition, the above-described area ratio in a case where there exist two or more second openings 82*o* as illustrated in FIG. 6 will be described. For example, first, as illustrated in FIG. 6, a case where two or more second openings 82*o* exist when viewed in the X-axis direction through which wind passes will be described. In this case, the area of each of the second openings 82*o* in the YZ plane is preferably 10% or more and 90% or less of the projected area described above. The above-described area ratios calculated from the respective second openings 82*o* may be different or the same as long as the area ratios are within a range of 10% or more and 90% or less.

Next, a case where two or more second openings 82*o* exist in the same YZ plane will be described. This is, for example, a case where a through hole having a further opening exists on the second member having the second d member 112*d* in FIG. 6. In this case, the sum of the areas of the openings on the second member having the second d member 112*d* is preferably 10% or more and 90% or less of the projected area described above. The above-described area ratios calculated from the sum of the areas of the openings on the second member having the second d member 112*d* and the sum of the areas of the openings on the other second member having the second c member 112*c* may be different or the same as long as they are within the range of 10% or more and 90% or less.

When the above-described area ratio is 10% or more, a speed of the gas entering the housing can be set to at least 10% or more of a speed of the gas entering from the outside, which is the area ratio, and a sufficient gas response speed can be achieved. On the other hand, when the area ratio described above is 90% or less, the amount of water vapor entering the inside of the housing through the first opening can be reduced, and deterioration of the dehumidifying effect by the electrochemical element can be suppressed. The above-mentioned value is preferably 30% or more and 70% or less in consideration of gas responsiveness and dehumidifying properties.

Figure 7:
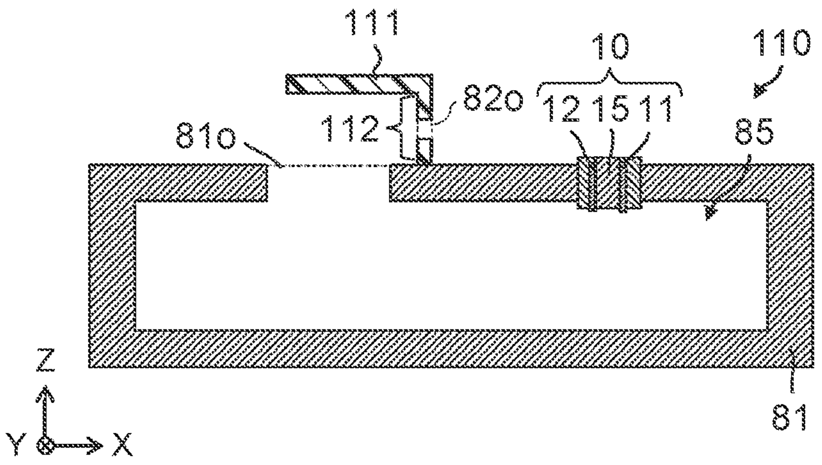
FIG. 7 is a schematic cross-sectional view illustrating another example of the electrochemical device according to the first embodiment.

FIG. 7 is a schematic cross-sectional view illustrating another example of the electrochemical device according to the first embodiment. FIG. 7 adopts the first member 111 and the second member 112 described with reference to FIG. 2. In addition, the electrochemical device of FIG. 7 has an electrochemical element 10.

The electrochemical element 10 includes a first electrode 11, a second electrode 12, and a third member 15. The third member 15 is provided between the first electrode 11 and the second electrode 12. For example, the third member 15 contains a polymer electrolyte. The third member 15 is, for example, a polymer electrolyte film.

The electrochemical element 10 can perform at least one of, for example, dehumidification, humidification, ozone generation, oxygen generation, oxygen removal, and hydrogen generation. By applying a voltage between the first electrode 11 and the second electrode 12, at least one of dehumidification, humidification, ozone generation, oxygen generation, oxygen removal, and hydrogen generation is possible.

Hereinafter, an example in which the electrochemical element 10 has a dehumidifying function will be described. Dehumidification is performed by applying the voltage between the first electrode 11 and the second electrode 12. For example, when the voltage is applied, moisture in the housing 81 is separated into hydrogen and oxygen by electrochemical decomposition, and released to the outside of the housing 81 through the third member 15. Accordingly, dehumidification is performed. The application of the voltage is performed, for example, by providing a battery. The electrochemical element 10 is, for example, a dehumidifying element.

For example, a voltage referenced to the second electrode 12 is applied to the first electrode 11. For example, when a voltage having a first polarity is applied to the first electrode 11, the electrochemical element 10 releases water to the outside of the housing 81 through the third member 15. Hereinafter, the first polarity is positive. Dehumidification is performed when the voltage having the first polarity is applied to the first electrode 11.

The electrochemical element 10 can release water in a space 85 in the housing 81 to the outside of the housing 81 through the third member 15. As a result, the space in the housing 81 is dehumidified. The housing 81 may contain, for example, a resin, a ceramic, a metal, and the like. The housing 81 may be made of, for example, a resin, a ceramic, a metal, or the like. The first member 111 and the second member 112 also may be made of, for example, a resin, a ceramic, a metal, or the like.

Figure 8:
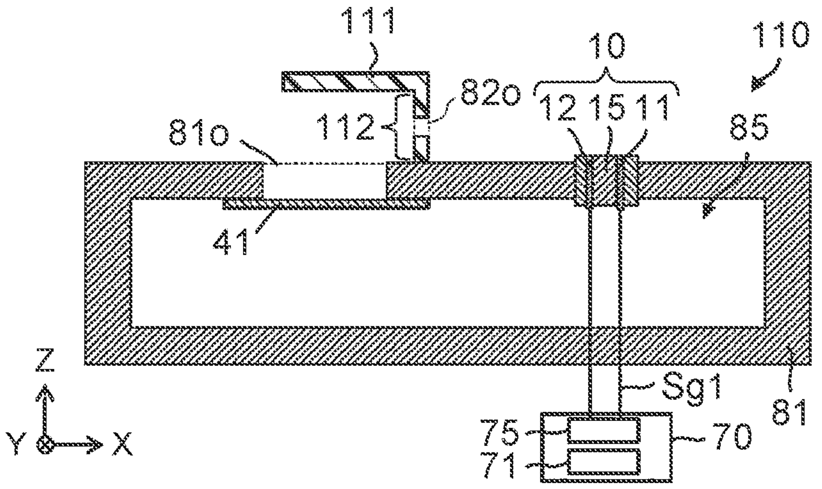
FIG. 8 is schematic a cross-sectional view illustrating still another example of the electrochemical device according to the first embodiment.

FIG. 8 is a schematic cross-sectional view illustrating still another example of the electrochemical device according to the first embodiment. The electrochemical device 110 in FIG. 8 further includes a first film 41 and a controller 70 in addition to the electrochemical device 110 in FIG. 7. The first film 41 is, for example, provided so as to cover the first opening 81*o*. As described later, the first film 41 is, for example, a porous film. The first film 41 does not substantially allow a liquid (for example, water) to permeate therethrough. For example, the first film 41 allows a gas (for example, hydrogen etc.) to permeate therethrough.

By providing the first film 41 in the first opening 81*o*, an influence of external humidity is suppressed in the space 85 in the housing 81. By an electrochemical action (for example, dehumidification) by the electrochemical element 10, the state of the space 85 becomes an intended state. As will be described later, by providing a detector or the like in the housing 81, the detector can be maintained in an intended state (for example, low humidity).

The controller 70 is electrically connected to the first electrode 11 and the second electrode 12. In this example, the controller 70 includes a circuit unit 75 and a first battery 71. The first battery 71 can supply power to the circuit unit 75. The circuit unit 75 can apply the voltage between the first electrode 11 and the second electrode 12. The voltage is, for example, a first signal Sg1. When the first signal Sg1 (voltage) is applied to the first electrode 11 and the second electrode 12, the electrochemical action (for example, dehumidification) in the electrochemical element 10 is performed.

In the embodiment, the electrochemical device 110 is driven by the first battery 71. This makes it possible to operate in a place where commercial power or the like is not supplied, and an application of the electrochemical device 110 and various equipments using the electrochemical device 10 is expanded. Since a capacity of the first battery 71 is fixed, it is desired to reduce power consumption in the electrochemical device 110 in order to prolong a driving time of the electrochemical device 110.

In general, the electrochemical element 10 is often driven by a DC signal (DC voltage) having a constant value. In this case, a DC current having a constant value flows in the electrochemical element 10. As a result, power is always consumed, thereby increasing power consumption.

In the embodiment, the voltage (first signal Sg1) supplied to the electrochemical element 10 is a duty signal. At this time, by setting the first signal Sg1 to a special waveform, it is possible to reduce power consumption while maintaining a high electrochemical action. A reason will be described later with reference to FIG. 9.

In the embodiment, the electrochemical element 10 includes a cathode and an anode. The cathode is one of the first electrode 11 and the second electrode 12. The anode is the other of the first electrode 11 and the second electrode 12.

For example, the cathode may include a cathode base and a cathode side catalyst member provided on a surface of the cathode base. The anode may include an anode base and an anode side catalyst member provided on a surface of the anode base. At least a part of a solid polymer electrolyte film is provided between the cathode side catalyst member and the anode side catalyst member. The solid polymer electrolyte film corresponds to the third member 15.

For example, the cathode base includes a carbon film (for example, carbon paper). The cathode side catalyst member contains carbon powder. Platinum adheres to a surface of the carbon powder. The carbon powder holds the platinum. For example, the anode base includes a titanium mesh. A platinum film is provided on a surface of the titanium mesh. The platinum film is formed by, for example, plating. The anode side catalyst member contains platinum particles and a fluororesin. The solid polymer electrolyte film contains a fluororesin. The fluororesin is, for example, a copolymer of a sulfonated tetrafluoroethylene-based fluororesin.

Figure 9:
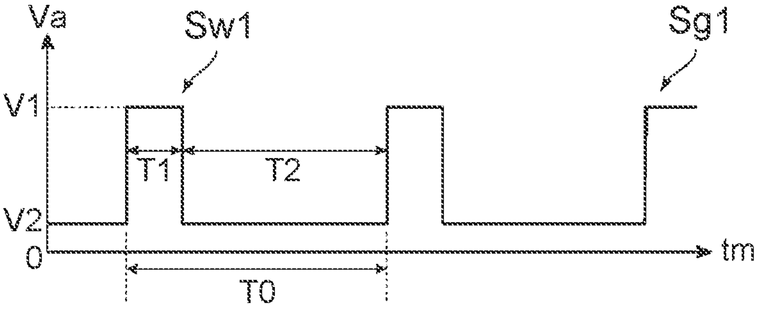
FIG. 9 is a schematic view illustrating an operation of the electrochemical device.

Next, an example of the first signal Sg1 will be described with reference to FIG. 9. FIG. 9 illustrates the first signal Sg1. The horizontal axis in FIG. 9 represents a time tm. The vertical axis represents a voltage Va between the first electrode 11 and the second electrode 12. The voltage Va is a potential referenced to a potential of the second electrode 12.

As illustrated in FIG. 9, the first signal Sg1 includes a waveform Sw1 that repeats in a first period T0. The waveform Sw1 includes a first period T1 and a second period T2. In the first period T1, the voltage Va is a first voltage V1 of the first polarity. In the second period T2, the voltage Va is a second voltage V2 of the first polarity. The first polarity is either positive or negative. In this example, the first polarity is positive. The first voltage V1 and the second voltage V2 are positive. An absolute value of the second voltage V2 is smaller than an absolute value of the first voltage V1.

In one example, the first voltage V1 is 2.5 V or more and 3.5 V or less. In one example, the second voltage V2 is 0.5 V or more and 1.5 V or less. As described above, since the second voltage V2 of the low voltage is also the first polarity (positive) and is not 0 voltage, a current flowing in a transition period from the first period T1 of the high voltage (first voltage V1) to the second period T2 of the low voltage (second voltage V2) hardly becomes a negative current. The current flowing in the transition period described above is a positive current, and even if the current flowing in the transition period is negative, the absolute value thereof is small. As a result, a reverse reaction in the electrochemical action, that is, a reaction in which moisture is released from the third member 15 into the housing 81, is suppressed. In addition, by providing the second period T2 of the low-voltage second voltage V2, it is possible to reduce power consumption while maintaining the intended high electrochemical action (for example, dehumidification) in such a first signal Sg1.

Figure 10A:
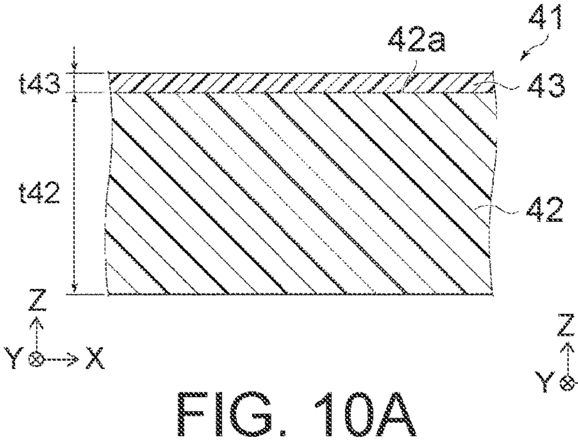
FIG. 10A and FIG. 10B are schematic cross-sectional views illustrating a first film that can be included in the electrochemical device according to the first embodiment.
Figure 10B:
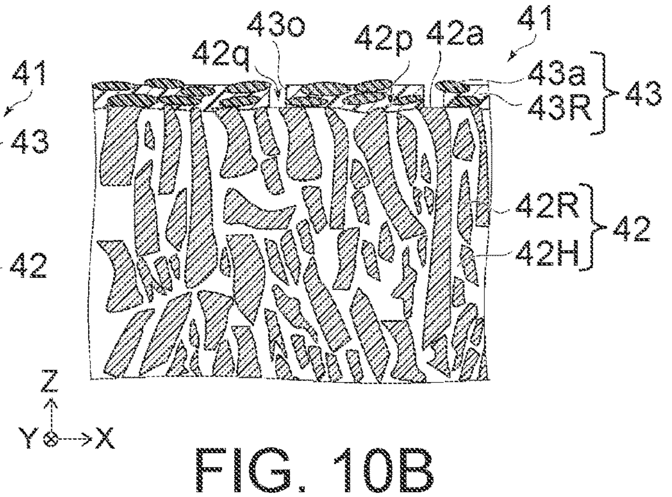

Next, the first film that can be included in the electrochemical device according to the embodiment will be described. FIGS. 10A and 10B are schematic cross-sectional views illustrating the first film that can be included in the electrochemical device according to the first embodiment. As illustrated in FIG. 10A, the first film 41 may include a first layer 42 and a second layer 43. A direction from the first layer 42 to the second layer 43 is defined as the Z-axis direction. One direction perpendicular to the Z-axis direction is defined as the X-axis direction. A direction perpendicular to the Z-axis direction and the X-axis direction is defined as the Y-axis direction. The first layer 42 and the second layer 43 extend along the X-Y plane.

As illustrated in FIG. 10B, the first layer 42 includes a first resin 42R. The first resin 42R is provided with a plurality of holes 42H. The first layer 42 is, for example, a porous layer.

The first layer 42 includes a first surface 42*a*. The first surface 42*a* is a surface facing the second layer 43. At least a part of the plurality of holes 42H reaches the first surface 42*a*.

The second layer 43 is provided on the first surface 42*a* of the first layer 42. The second layer 43 includes a second resin 43R. The second resin 43R blocks at least a part of the plurality of holes 42H reaching the first surface 42*a*. The second layer 43 is, for example, an ineffective void layer (independent void layer). A part of the second resin 43R may be provided in a portion close to the surface of the hole 42H.

In the embodiment, the porous first layer 42 and the second resin 43R (second layer 43) that blocks a part of the plurality of holes 42H of the first layer 42 are provided. For example, another part of the plurality of holes 42H of the first layer 42 is not blocked by the second resin 43R.

The hole 42H not blocked by the second resin 43R allows a target gas to pass through the first film 41. The target gas is, for example, hydrogen. On the other hand, since a part of the plurality of holes 42H is blocked by the second resin 43R, a non-target substance does not pass through the first film 41. Non-target substances include, for example, liquids (such as water and oil). According to the embodiment, the target gas can efficiently permeate.

Due to the first film 41 that can be included in the electrochemical device according to the embodiment, for example, high water repellency can be obtained. For example, high air permeability can be obtained. For example, high chemical resistance can be obtained. For example, high corrosion resistance can be obtained. For example, high dustproofness can be obtained. For example, entry of water or oil is suppressed. For example, high reliability can be obtained.

In the embodiment, the first resin 42R preferably contains a fluorine compound. The first resin 42R contains, for example, polytetrafluoroethylene (PTFE). Stable permeability can be obtained. Permeation of water or the like can be effectively suppressed.

The second resin 43R contains, for example, an acrylic resin. As a result, at least a part of the plurality of holes 42H is stably blocked. For example, permeation of a non-target substance can be stably suppressed.

The thickness of the first layer 42 is defined as a first thickness t42. The thickness of the second layer 43 is defined as a second thickness t43. These thicknesses are lengths along the Z-axis direction. In the embodiment, for example, the first thickness t42 is thicker than the second thickness t43. In one example, the first thickness t42 is at least twice as thick as the second thickness t43. For example, the first thickness t42 may be no more than 10,000 times thicker than the second thickness t43. For example, permeability of the target gas and suppression of permeation of a non-target substance can be appropriately obtained.

The first thickness t42 of the first layer 42 is, for example, 10 μm or more and 5,000 μm or less. The first thickness t42 may be, for example, 1,000 μm or less. The second thickness t43 of the second layer 43 is, for example, 0.1 μm or more and 100 μm or less. When a part of the second resin 43R is provided in the portion close to the surface of the hole 42H, the thickness of the second resin 43R provided in the portion close to the surface of the hole 42H may be, for example, 0.1 μm or more and 5 μm or less.

The second resin 43R covers at least a part of the first surface 42*a*. As illustrated in FIG. 10B, the first surface 42*a* includes a first region 42*p* in which the second resin 43R is provided and a second region 42*q* in which the second resin

43R is not provided. A ratio of the area of the first region 42*p* to the area of the second region 42*q* is 0.01 or more and 100 or less.

For example, the second resin 43R may include an opening 43*o*. The second region 42*q* where the second resin 43R is not provided corresponds to the opening 43*o*. An opening ratio may be, for example, 1% or more and 99% or less.

As illustrated in FIG. 10B, in this example, the second layer 43 further includes a plurality of first solid pieces 43*a*. The plurality of first solid pieces 43*a* are fixed by the second resin 43R. The plurality of first solid pieces 43*a* contain, for example, at least one of a metal, a metal oxide, and a metal nitride. For example, the plurality of first solid pieces 43*a* contain Fe, Cr, and Ni. The plurality of first solid pieces 43*a* contain, for example, steel use stainless (SUS). For example, high corrosion resistance can be obtained. The plurality of first solid pieces 43*a* may contain, for example, titanium oxide.

An average size (length) of one of the plurality of first solid pieces 43*a* is, for example, 0.1 μm or more and 10 μm or less.

As described above, the electrochemical device according to the first embodiment has the housing, the first member, the second member existing between the housing and the first member, and the first opening facing the first member. At least a part of the second member is provided on the housing, and the second member has the second opening. This makes it possible to improve the characteristics of the electrochemical device.

Second Embodiment

According to a second embodiment, a sensor including the electrochemical device according to the first embodiment and a detector provided inside the housing, is provided.

Figure 11:
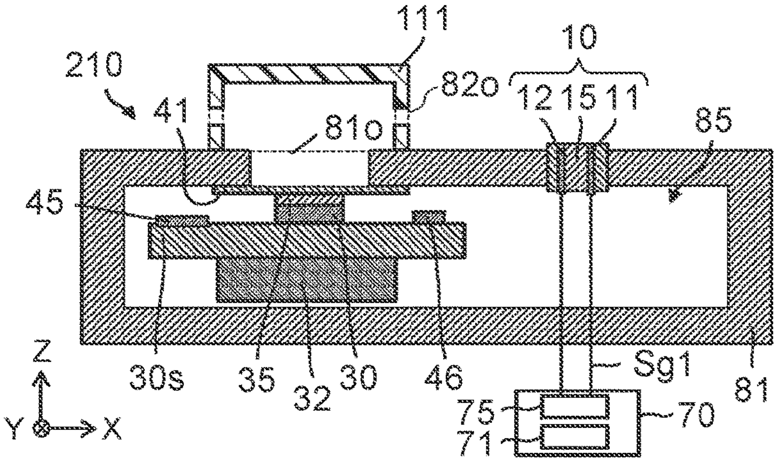
FIG. 11 is a schematic cross-sectional view illustrating a sensor according to a second embodiment.

FIG. 11 is a schematic cross-sectional view illustrating the sensor according to the second embodiment. As illustrated in FIG. 11, a sensor 210 according to the embodiment includes the electrochemical device 110 according to the first embodiment and a detector 30. The electrochemical device 110 includes the first member 111 and the housing 81. The detector 30 is provided inside the housing 81. The detector 30 can detect at least one selected from a group consisting of hydrogen, oxygen, and volatile organic compounds (VOCs). The detector 30 may be referred to as a gas detector or a substance detector.

In this example, the sensor 210 includes the first film 41. The first film 41 is provided between the detector 30 and the first opening 81*o* of the housing 81. At least a part of the first film 41 is porous. The first film 41 contains, for example, a resin containing fluorine. The first film 41 contains, for example, polytetrafluoroethylene (PTFE). For example, the first film 41 does not allow a liquid (such as water) to permeate therethrough. The first film 41 allows a gas (for example, hydrogen, oxygen or VOCs) to be detected by the detector 30 to pass therethrough.

In the sensor 210 according to the embodiment, the detector 30 is provided inside the electrochemical device 110 according to the first embodiment. For example, when humidity in the environment around the detector 30 changes, a detection value of a detection target in the detector 30 is affected. By using this detection value to maintain the humidity in the environment around the detector 30 in a target range, it is possible to suppress deterioration or failure of the sensing function due to exposure of the sensor and the sensor circuit for a long time in a high-humidity environment. This makes it possible to detect hydrogen, oxygen and/or VOCs with higher accuracy.

In the embodiment, the first film 41 may be in contact with the detector 30. Alternatively, the distance between the first film 41 and the detector 30 is 1 cm or less. By providing the detector 30 near the first film 41, the detection target gas that has passed through the first film 41 can be detected with higher accuracy.

In the embodiment, the distance between the electrochemical element 10 and the detector 30 is preferably short. For example, the detector 30 is preferably fixed the near the electrochemical element 10. The distance between the electrochemical element 10 and the detector 30 is, for example, 1 mm or more and 50 mm or less.

As illustrated in FIG. 11, the sensor 210 may include a second battery 32. The second battery 32 can supply power to the detector 30. By providing the second battery 32, for example, a detection target can be detected even in a place where commercial power is not supplied.

In the sensor 210, the detector 30 is provided on a substrate 30*s*. A lid 35 may be provided between the detector 30 and the first film 41. A humidity sensor 46 may be provided on the substrate 30*s*. The humidity sensor 46 may monitor humidity in the space 85 inside the housing 81.

The sensor 210 may include a communication unit 45. The communication unit 45 can transmit information regarding a detection result of the detector 30 to an external device. The detection result includes, for example, information (data) related to a concentration of the detection target. The transmission may be performed, for example, in at least one of a wired or a wireless manner. The communication unit 45, for example, is a communication circuit.

The sensor according to the second embodiment is the sensor including the electrochemical device described in the first embodiment and the detector provided inside the housing. Since the sensor according to the second embodiment includes the electrochemical device described in the first embodiment, it is possible to realize a sensor with improved performance.

Third Embodiment

According to a third embodiment, there is provided a sensor system including the sensor according to the second embodiment and a processing device, in which the sensor includes a communication unit, and the processing device can process information based on a signal obtained from the communication unit.

Figure 12:
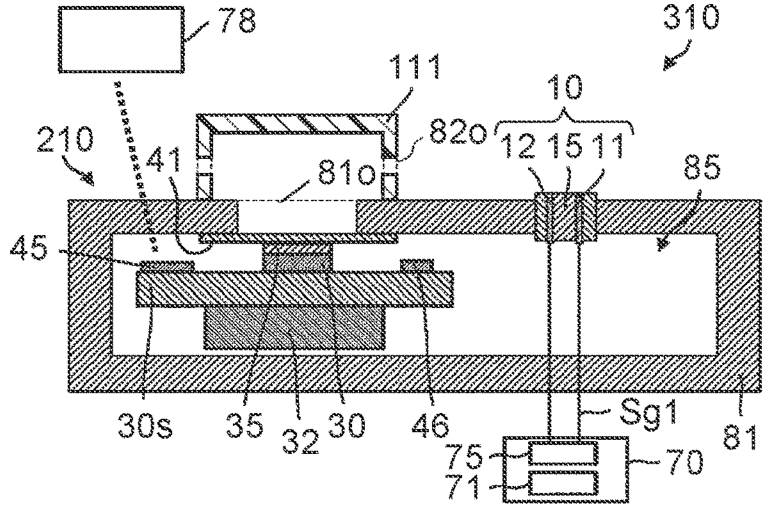
FIG. 12 is a schematic cross-sectional view illustrating a sensor according to a third embodiment.

FIG. 12 is a schematic cross-sectional view illustrating the sensor according to the third embodiment. As illustrated in FIG. 12, a sensor system 310 according to the embodiment includes the sensor 210 according to the second embodiment and a processing device 78. The processing device 78 may include, for example, a computer. The sensor 210 includes the communication unit 45. The processing device 78 can process information based on the signal obtained from the communication unit 45. The signal obtained from the communication unit 45 may include, for example, information (data) related to the detection result of the detector 30.

The processing of the information (detection result) in the processing device 78 may include, for example, saving of the information (detection result). The processing of the information (detection result) may include, for example, a comparison between the information (detection result) and a reference value. The processing device 78 may output an alert or the like according to a result of the comparison. The processing of the information (detection result) may include, for example, an arbitrary calculation related to the information (detection result). The calculation may include, for example, derivation of a maximum value, or the like, or derivation of an average value, or the like.

The sensor system according to the third embodiment includes the sensor according to the second embodiment and the processing device, in which the sensor includes the communication unit, and the processing device can process information based on the signal obtained from the communication unit.

EXAMPLES

Hereinafter, examples of results of experiments performed by the inventors will be described. In the first and second experiments, the characteristics of the humidity sensor in the housing at 90% relative humidity (RH) under environmental humidity are shown. A porous PTFE film was used as the first film, and a ratio of the area of the second opening to the area of a surface of the second member parallel to the direction intersecting the surface of the housing where the first opening exists (the ratio of the second opening to the second member) was as illustrated in Tables 1 and 2 in each of Examples 1 to 10 and Comparative Examples 1 and 2. Table 1 illustrates the results of the first experiment when no wind was generated around the housing.

TABLE 1

| First experiment (with no wind) | Area ratio of second opening [%] | Humidity by humidity sensor [% RH] |
|---|---|---|
| Example 1 | 10 | 30 |
| Example 2 | 30 | 37 |
| Example 3 | 40 | 40 |
| Example 4 | 70 | 50 |
| Example 5 | 90 | 53 |
| Comparative Example 1 | — | 55 |

The result of the first experiment shows that the humidity inside the housing can be reduced by providing the second opening in the electrochemical device.

Next, the results of the second experiment in which wind was generated around the housing are illustrated in Table 2. The wind speed was 0.5 to 1 m/sec.

TABLE 2

| Second experiment (with wind) | Area ratio of second opening [%] | Humidity by humidity sensor [% RH] |
|---|---|---|
| Example 6 | 10 | 40 |
| Example 7 | 30 | 47 |
| Example 8 | 40 | 50 |
| Example 9 | 70 | 60 |
| Example 10 | 90 | 63 |
| Comparative Example 2 | — | 65 |

The result of the second experiment shows that the humidity inside the housing can be reduced by providing the second opening in the electrochemical device.

From the first experiment and the second experiment, it is found that the humidity can be lowered in both cases by providing the second opening in the electrochemical device.

Although some embodiments of the present invention have been described, these embodiments have been presented as examples, and are not intended to limit the scope of the invention. These novel embodiments can be implemented in various other forms, and various omissions, substitutions, and changes can be made without departing from the gist of the invention. These embodiments and modifications thereof are included in the scope and gist of the invention, and are included in the invention described in the scope of the claims and the equivalent scope thereof.

Hereinafter, the invention according to the embodiment will be additionally described.

[1] An electrochemical device having a housing, a first member, and a second member provided between the housing and the first member, in which the housing has a first through hole including a first opening that faces the first member, and the second member has a second through hole including a second opening.

[2] The electrochemical device according to [1], in which there exist at least two or more of the second through holes.

[3] The electrochemical device according to [1] or [2], in which the first member has a lower surface facing the housing and an upper surface facing the lower surface, and when the second opening and a space between the first member and the housing having the first opening are projected in a normal direction of the second opening, a projected area of the second opening is 10% or more and 90% or less of a projected area of the space.

[4] The electrochemical device according to any one of [1] to [3], in which the electrochemical device has an electrochemical element.

[5] The electrochemical device according to any one of [1] to [4], in which the electrochemical element is a dehumidifying element.

[6] A sensor including the electrochemical device according to any one of [1] to [5], and a detector provided inside the housing.

[7] The sensor according to any one of [1] to [6], in which the detector is a gas detector.

[8] The sensor according to any one of [6] or [7], further including a battery capable of supplying electric power to the detector.

[9] A sensor system including the sensor according to any one of [6] to [8], and a processing device, in which the sensor includes a communication unit, and the processing device is capable of processing information based on a signal obtained from the communication unit.

[10] A sensor including an electrochemical device including a housing, a first member, and a second member provided between the housing and the first member, in which the housing has a first through hole including a first opening that faces the first member, the second member has a second through hole including a second opening, in which the electrochemical device has an electrochemical element, and the electrochemical device includes a detector provided in the housing.

[11] The sensor according to [10], in which there exist at least two or more of the second through holes.

[12] The sensor according to any one of [10] or [11], in which when the second opening and a space between the first member and the housing having the first opening are projected in a normal direction of the second opening, a projected area of the second opening is 10% or more and 90% or less of a projected area of the space.

[13] The sensor according to any one of [10] to [12], further including a battery capable of supplying electric power to the detector.

[14] The sensor according to any one of [10] to [13], including a communication unit, in which the communication unit transmits information of the detector to an external processing device.

[15] The sensor according to any one of [10] to [14], in which the electrochemical element is a dehumidifying element.

[16] The sensor according to any one of [10] to [15], in which the detector is a gas detector.

What is claimed is:

1. A sensor comprising:

a housing having a first part, a second part, and a third part, the third part being positioned between the first part and the second part in a first direction, a first through hole piecing the third part in a second direction crossing the first direction, the first through hole including a first opening;

a first member including a first region facing the first part in the second direction, a second region facing the second part in the second direction, and a third region facing the third part in the second direction;

a second member including a first portion that is in direct contact with the first part, a second portion that is in direct contact with the second part, a third portion connected to the first region, and a fourth portion connected to the second region, a second through hole being provided between the first portion and the third portion, a third through hole being provided between the second portion and the fourth portion, a direction from the second through hole to the third through hole being along the first direction, a position of the third portion in the second direction being between a position of the first portion in the second direction and a position of the first region in the second direction, a position of the fourth portion in the second direction being between a position of the second portion in the second direction and the position of the second region in the second direction;

a gas detector provided in the housing; and a first film provided between the first opening and the gas detector, wherein the first member has a lower surface facing the housing and an upper surface, the lower surface being positioned between the housing and the upper surface in the second direction and when the second opening and a space between the first member and the housing having the first opening are projected in a normal direction of the second opening, a projected area of the second opening is 10% or more and 90% or less of a projected area of the space, and the first film has a first layer and a second layer, the first film including a first resin, a plurality of holes being provided in the first resin, the first layer including a first face, at least a part of the plurality of holes reaching the first face; and the second layer including a second resin, the second resin blocking at least a part of the plurality of holes reaching the first face.

2. The sensor according to claim 1, wherein the sensor has an electrochemical element.

3. The sensor according to claim 2, wherein the electrochemical element is a dehumidifying element.

4. The sensor according to claim 1, further comprising a battery capable of supplying electric power to the gas detector.

5. A sensor system comprising:

the sensor according to claim 1; and a processing device, wherein the sensor includes a communication unit, and the processing device is capable of processing information based on a signal obtained from the communication unit.

* * * * *